(12) United States Patent
Takagi et al.

(10) Patent No.: US 9,371,540 B2
(45) Date of Patent: Jun. 21, 2016

(54) METHOD FOR PRODUCTION OF PLANT IMPARTED WITH STRESS TOLERANCE AND USE THEREOF

(71) Applicants: National Institute of Advanced Industrial Science and Technology, Tokyo (JP); GreenSogna, Inc., Tsukuba-shi, Ibaraki (JP)

(72) Inventors: Masaru Takagi, Tsukuba (JP); Tomomi Mito, Tsukuba (JP); Kyoko Matsui, Ryugasaki (JP)

(73) Assignees: NATIONAL INSTITUTE OF ADVANCED INDUSTRIAL SCIENCE AND TECHNOLOGY, Tokyo (JP); GREENSOGNA, INC., Ibaraki (JP)

( * ) Notice: Subject to any disclaimer, the term of this patent is extended or adjusted under 35 U.S.C. 154(b) by 251 days.

(21) Appl. No.: 13/936,346

(22) Filed: Jul. 8, 2013

(65) Prior Publication Data
US 2013/0291221 A1   Oct. 31, 2013

Related U.S. Application Data

(63) Continuation of application No. 13/121,165, filed as application No. PCT/JP2009/065385 on Sep. 3, 2009, now abandoned.

(30) Foreign Application Priority Data

Sep. 29, 2008 (JP) .................................. 2008-251043

(51) Int. Cl.
C12N 15/62 (2006.01)
C12N 15/82 (2006.01)

(52) U.S. Cl.
CPC ............ *C12N 15/8273* (2013.01); *C12N 15/62* (2013.01); *C12N 15/8216* (2013.01); *C12N 15/8271* (2013.01)

(58) Field of Classification Search
None
See application file for complete search history.

(56) References Cited

U.S. PATENT DOCUMENTS

| | | |
|---|---|---|
| 2003/0061637 A1 | 3/2003 | Jiang et al. |
| 2003/0114657 A1 | 6/2003 | Mikoshiba et al. |
| 2004/0019927 A1 | 1/2004 | Sherman et al. |
| 2004/0045049 A1 | 3/2004 | Zhang et al. |
| 2006/0272060 A1 | 11/2006 | Heard et al. |
| 2008/0301836 A1* | 12/2008 | Century et al. ............... 800/279 |

FOREIGN PATENT DOCUMENTS

| | | |
|---|---|---|
| EP | 1033405 | 9/2000 |
| JP | 2001-186879 | 7/2001 |
| JP | 2001-269176 A | 10/2001 |
| JP | 2001-269177 A | 10/2001 |
| JP | 2001-269178 A | 10/2001 |
| JP | 2001-269179 A | 10/2001 |
| JP | 2001-292776 A | 10/2001 |
| JP | 2001-292777 A | 10/2001 |
| JP | 2001-292778 | 10/2001 |
| JP | 2001-292779 | 10/2001 |
| JP | 2005-013214 A | 1/2005 |
| JP | 2005-027654 A | 2/2005 |
| JP | 2005-204573 A | 8/2005 |
| JP | 2005-204657 | 8/2005 |
| JP | 2006-006248 A | 1/2006 |
| JP | 2006-020607 A | 1/2006 |
| WO | 01/35726 | 5/2001 |
| WO | 02/15675 | 2/2002 |
| WO | 2004/058980 | 7/2004 |
| WO | 2005/047516 | 5/2005 |
| WO | 2007/044043 | 4/2007 |
| WO | 2008/041693 | 4/2008 |

OTHER PUBLICATIONS

Devaiah et al. Phosphate homeostasis and root development in Arabidopsis are synchronized by the zinc finger transcription factor ZAT6. Plant Physiology. 2007. 145: 147-159.*

Mito et al. Generation of chimeric repressors that confer salt tolerance in Arabidosis and rice. Plant Biotechnology Journal. 2011. 9: 736-746.*

Shikata et al. The utility of transcripton factors for manipulation of floral traits. Plant Biotechnology. 2008. 25: 31-36.*

Heard J.E. et al., G545, G350, Publication Site for Issued and Published Sequences (PSIPS) [online], Nov. 2006, United States Patent and Trademark Office, [retrieved on Dec. 8, 2014], retrieved from the internet: <URL: http://seqdata.uspto.gov/?pageRequest=viewSequence&DocID=2006272060 &seqID=425%2C426%2C592>, Seq ID No. 425,426,591,592.

Zhang J. et al., G545, Publication Site for Issued and Published Sequences (PSIPS) [online], Mar. 2004; United States Patent and Trademark Office, [retrieved on Dec. 8, 2014] retrieved from the internet: <URL: http://seqdata.uspto.gov/?pageRequest=viewSequence&DocID=20040045049&seqID=345%2C346%2C1762%2C1763>, Seq ID No. 345,346,1762,1763.

Sherman B.K. et al., G545, G350 Paralogous to G545, Publication Site for Issued and Published Sequences (PSIPS) [online], Jan. 2004; United States Patent and Trademark Office, [retrieved on Dec. 8, 2014] retrieved from the internet: <URL: http://seqdata.uspto.gov/?pageRequest=viewSequence&DocID=20040019927 &seqID=103%2C104%2C1987%2C1988>, Seq ID No. 103,104,1987,1988.

(Continued)

*Primary Examiner* — Shubo (Joe) Zhou
*Assistant Examiner* — Ashley K Buran
(74) *Attorney, Agent, or Firm* — Casimir Jones, S.C.

(57) ABSTRACT

The present invention provides a method for producing a plant with a stress tolerance, comprising the step of inhibiting, in a plant, a function of a first polypeptide including an amino acid sequence represented by any one of SEQ ID NOS: 2, 4, 6, 8, and 10. This enables developing a new technique capable of producing a plant with a stress tolerance such as a salt tolerance and a high osmotic pressure tolerance.

1 Claim, 1 Drawing Sheet

(56) References Cited

OTHER PUBLICATIONS

Office Action mailed May 21, 2013, JP Patent Application No. 2010-530804 (JP National Phase Entry of PCT/JP2009/065385) (English translation attached).

International Search Report dated Nov. 17, 2009 from International Patent Application No. PCT/JP2009/065385.

Zhu et al., (1998) "Genetic Analysis of Salt Tolerance in Arabidopsis: Evidence for a Critical Role of Potassium Nutrition." The Plant Cell, 10: 1181-1191.

Mittler et al., (2006) "Gain- and loss-of-function mutations in Zat10 enhance the tolerance of plants to abiotic stress." FEBS Lett., 580:6537-6542.

Kasuga et al., (1999) "Improving plant drought, salt, and freezing tolerance by gene transfer of a single stress-inducible transcription factor." Nat. Biotechnol., 17:287-291.

Ciftci-Yilmaz et al., (2007) "The EAR-motif of the Cys2/His2-type Zinc Finger Protein Zat7 Plays a Key Role in the Defense Response of Arabidopsis to Salinity Stress." J. Biol. Chem., 282:9260-9268.

Ohta et al., (2001) "Repression Domains of Class II ERF Transcriptional Repressors Share an Essential Motif for Active Repression." The Plant Cell, 13:1959-1968.

Hiratsu et al., (2002) "The Superman protein is an active repressor whose carboxy-terminal repression domain is required for the development of normal flowers." FEBS Letters, 514:351-354.

Koyama et al., (2007) "TCP Transcription Factors Control the Morphology of Shoot Lateral Organs via Negative Regulation of the Expression of Boundary-Specific Genes in Arabidoptsis." The Plant Cell, 19:473-484.

Denekamp et al., (2003) "Integration of Wounding and Osmotic Stress Signals Determines the Expression of the AtMYB102 Transcription Factor Gene." Plant Physiol., 132(3):1415-1423.

Devaiah et al., (2007) Phosphate Homeostasis and Root Development in Arabidopsis Are Synchronized by the Zinc Finger Transcription Factor ZAT61. Plant Physiol., 145:147-159.

Fujimoto et al., "Arabidopsis Ethylene-Responsive Element Binding Factors Act as Transcriptional Activators or Repressors of GCC Box-Mediated Gene Expression." The Plant Cell, 12:393-404.

De Vos et al., (2006) "The Arabidopsis thaliana Transcription Factor AtMYB102 Functions in Defense Against the Insect Herbivore Pieris rapae." Plant Signal Behav., 1(6): 305-311.

Valdes-Lopez et al., (2008) "Transcriptional Regulation and Signaling in Phosphorus Starvation: What About Legumes?" J. Integ. Plant Biol., 50(10):1213-1222.

Herbette et al., (2006) "Genome-wide transcriptome profiling of the early cadmium response of Arabidopsis roots and shoots." Biochemie, 88(11):1751-1765.

Yang et al., (2007) "Transcriptional profiling of canola (*Brassica napus* L.) responses to the fungal pathogen *Sclerotinia sclerotiorum*." Plant Science, 173:156-171.

Mito et al., (2009) "Isolation of the Arabidopsis plants expressing chimeric repressors, which show tolerance to abiotic stresses." The proceedings of the 50th annual meeting of the Japanese Society of Plant Physiologists, 50th: 339.

U.S. Office Action mailed Apr. 8, 2013, U.S. Appl. No. 13/121,165.

U.S. Office Action mailed May 22, 2013, U.S. Appl. No. 13/121,165.

Zhang, et al., "A rice WRKY gene encodes a transcriptional repressor of the Gibberellin signaling pathway in aleurone cells," Plant Physiology. 2004. 134(4): 1500-1513.

Hiratsu, et al., "The Superman protein is an active repressor whose carboxyl-terminal repression domain is required for the development of normal flowers," FEBS. 2002. 514: 351-354.

Mittler, et al., "Gain- and loss-of-function mutations in Zat10 enhance the tolerance of plants to abiotic stress," FEBS. 2006. 580: 6537-6542.

Schulze et al., Environment as stress factor: stress physiology of plants. Plant Ecology. 2005. 702: 7-11.

Jonak, et al., "Stress signaling in plants: a mitogen-activated protein kinase pathway is activated by cold and drought," PNAS. 1996. 93: 11274-11279.

GenBank Accession No. NM_120516. Direct Submission. Published May 22, 2008.

Hommel, et al., Over-expression of a chimeric gene of the transcriptional co-activator MBF1 fused to the EAR repressor motif causes developmental alteration in Arabidopsis and tomato. Plant Science. 2008. 175: 168-177.

\* cited by examiner

SEQUENCE LISTING

```
<160> NUMBER OF SEQ ID NOS: 32

<210> SEQ ID NO 1
<211> LENGTH: 1053
<212> TYPE: DNA
<213> ORGANISM: Arabidopsis thaliana

<400> SEQUENCE: 1
atggcaaggt caccttgttg cgagaagaac ggactcaaga aagggccttg gacatctgaa      60
gaagaccaga agcttgttga ctatatccag aaacatggtt atggtaactg gagaaccctc     120
cccaaaaatg ccggtttgca aagatgtggc aaaagttgta ggttaaggtg gactaattat     180
ctccgaccag atataaagcg aggaaggttc tcttttgagg aagaagaaac cattattcag     240
cttcatagct tcttaggaaa caagtggtct gcgattgcgg cgcgtttacc aggaagaaca     300
gataatgaga tcaagaactt ttggaacact catataagaa agaagctact tagaatgggg     360
attgatccag tgactcacag tccacgactc gatctcctcg atatctcatc catcttagct     420
tcatctctat acaattcatc ttcacatcac atgaacatgt caagactcat gatggatact     480
aatcgtcgtc atcaccagca acatccattg gttaaccccg agatactcaa gctcgctacc     540
tctctcttct ctcaaaatca aaaccaaaac cttgtggtgg atcatgactc gagaactcaa     600
gagaagcaaa cagtttatag ccaaaccgga gtaaaccaat accaaaccaa ccaatatttc     660
gagaacacga ttactcaaga actccaatct tccatgccac cattccccaa tgaagctcgt     720
cagtttaaca acatggatca tcacttcaat ggttttggag aacaaaatct tgtttcaact     780
```

```
tctactacgt cagtccaaga ttgctataat ccgtcattca acgattattc aagttcaaat    840
tttgtcttgg atccttctta ttcggatcag agcttcaact tcgcaaattc ggtcttaaac    900
acgccatcct cgagcccgag cccgactacg ttaaactcga gttacatcaa tagtagcagt    960
tgcagcactg aggatgaaat agaaagctat tgcagtaatc tcatgaagtt tgatattccc   1020
gatttcttgg acgttaatgg ttttattata taa                                1053
```

<210> SEQ ID NO 2
<211> LENGTH: 350
<212> TYPE: PRT
<213> ORGANISM: Arabidopsis thaliana

<400> SEQUENCE: 2

```
Met Ala Arg Ser Pro Cys Cys Glu Lys Asn Gly Leu Lys Lys Gly Pro
1               5                   10                  15

Trp Thr Ser Glu Glu Asp Gln Lys Leu Val Asp Tyr Ile Gln Lys His
                20                  25                  30

Gly Tyr Gly Asn Trp Arg Thr Leu Pro Lys Asn Ala Gly Leu Gln Arg
            35                  40                  45

Cys Gly Lys Ser Cys Arg Leu Arg Trp Thr Asn Tyr Leu Arg Pro Asp
    50                  55                  60

Ile Lys Arg Gly Arg Phe Ser Phe Glu Glu Glu Thr Ile Ile Gln
65                  70                  75                  80

Leu His Ser Phe Leu Gly Asn Lys Trp Ser Ala Ile Ala Ala Arg Leu
                85                  90                  95

Pro Gly Arg Thr Asp Asn Glu Ile Lys Asn Phe Trp Asn Thr His Ile
            100                 105                 110

Arg Lys Lys Leu Leu Arg Met Gly Ile Asp Pro Val Thr His Ser Pro
        115                 120                 125

Arg Leu Asp Leu Leu Asp Ile Ser Ser Ile Leu Ala Ser Ser Leu Tyr
    130                 135                 140

Asn Ser Ser Ser His His Met Asn Met Ser Arg Leu Met Met Asp Thr
145                 150                 155                 160

Asn Arg Arg His His Gln Gln His Pro Leu Val Asn Pro Glu Ile Leu
                165                 170                 175

Lys Leu Ala Thr Ser Leu Phe Ser Gln Asn Gln Asn Gln Asn Leu Val
            180                 185                 190

Val Asp His Asp Ser Arg Thr Gln Glu Lys Gln Thr Val Tyr Ser Gln
        195                 200                 205

Thr Gly Val Asn Gln Tyr Gln Thr Asn Gln Tyr Phe Glu Asn Thr Ile
    210                 215                 220

Thr Gln Glu Leu Gln Ser Ser Met Pro Pro Phe Pro Asn Glu Ala Arg
225                 230                 235                 240

Gln Phe Asn Asn Met Asp His His Phe Asn Gly Phe Gly Glu Gln Asn
                245                 250                 255

Leu Val Ser Thr Ser Thr Ser Val Gln Asp Cys Tyr Asn Pro Ser
            260                 265                 270

Phe Asn Asp Tyr Ser Ser Ser Asn Phe Val Leu Asp Pro Ser Tyr Ser
        275                 280                 285

Asp Gln Ser Phe Asn Phe Ala Asn Ser Val Leu Asn Thr Pro Ser Ser
    290                 295                 300

Ser Pro Ser Pro Thr Thr Leu Asn Ser Ser Tyr Ile Asn Ser Ser Ser
305                 310                 315                 320
```

Cys Ser Thr Glu Asp Glu Ile Glu Ser Tyr Cys Ser Asn Leu Met Lys
                325                 330                 335

Phe Asp Ile Pro Asp Phe Leu Asp Val Asn Gly Phe Ile Ile
            340                 345                 350

<210> SEQ ID NO 3
<211> LENGTH: 1080
<212> TYPE: DNA
<213> ORGANISM: Arabidopsis thaliana

<400> SEQUENCE: 3

```
atgataagca aggatccaag atcgagttta cctccagggt ttcgatttca tccaacagat      60
gaagaactca ttctccatta cctaaggaag aaagtttcct cttccccagt cccgctttcg     120
attatcgccg atgtcgatat ctacaaatcc gatccatggg atttaccagc taaggctcca     180
tttggggaga aagagtggta ttttttcagt ccgagggata ggaaatatcc aaacggagca     240
agaccaaaca gagcagctgc gtctggatat tggaaagcaa ccggaacaga taaattgatt     300
gcggtaccaa atggtgaagg gtttcatgaa acattggta taaaaaagc tcttgtgttt      360
tatagaggaa agcctccaaa aggtgttaaa accaattgga tcatgcatga atatcgtctt     420
gccgattcat tatctcccaa aagaattaac tcttctagga gcggtggtag cgaagttaat     480
aataattttg gagataggaa ttctaaagaa tattcgatga gactggatga ttgggttctt     540
tgccggattt acaagaaatc acacgcttca ttgtcatcac ctgatgttgc tttggtcaca     600
agcaatcaag agcatgagga aaatgacaac gaaccattcg tagaccgcgg aacctttttg     660
ccaaatttgc aaaatgatca accccttaaa cgccagaagt cttcttgttc gttctcaaac     720
ttactagacg ctacagattt gacgtttctc gcaaattttc taaacgaaac cccggaaaat     780
cgttctgaat cagattttc tttcatgatt ggcaatttct ctaatcctga catttacgga     840
aaccattact ggatcagaa gttaccgcag ttgagctctc ccacttcaga gacaagcggc     900
atcggaagca aaagagagag agtggatttt gcggaagaaa cgataaacgc ttcgaagaag     960
atgatgaaca catatagtta caataatagt atagatcaaa tggatcatag tatgatgcaa    1020
caacctagtt tcctgaacca ggaactcatg atgagttctc accttcaata tcaaggctag    1080
```

<210> SEQ ID NO 4
<211> LENGTH: 359
<212> TYPE: PRT
<213> ORGANISM: Arabidopsis thaliana

<400> SEQUENCE: 4

Met Ile Ser Lys Asp Pro Arg Ser Leu Pro Gly Phe Arg Phe
1               5                   10                  15

His Pro Thr Asp Glu Glu Leu Ile Leu His Tyr Leu Arg Lys Val
            20                  25                  30

Ser Ser Ser Pro Val Pro Leu Ser Ile Ile Ala Asp Val Asp Ile Tyr
        35                  40                  45

Lys Ser Asp Pro Trp Asp Leu Pro Ala Lys Ala Pro Phe Gly Glu Lys
    50                  55                  60

Glu Trp Tyr Phe Phe Ser Pro Arg Asp Arg Lys Tyr Pro Asn Gly Ala
65                  70                  75                  80

Arg Pro Asn Arg Ala Ala Ala Ser Gly Tyr Trp Lys Ala Thr Gly Thr
                85                  90                  95

Asp Lys Leu Ile Ala Val Pro Asn Gly Glu Gly Phe His Glu Asn Ile
            100                 105                 110

```
Gly Ile Lys Lys Ala Leu Val Phe Tyr Arg Gly Lys Pro Lys Gly
            115                 120                 125

Val Lys Thr Asn Trp Ile Met His Glu Tyr Arg Leu Ala Asp Ser Leu
    130                 135                 140

Ser Pro Lys Arg Ile Asn Ser Ser Arg Ser Gly Ser Glu Val Asn
145                 150                 155                 160

Asn Asn Phe Gly Asp Arg Asn Ser Lys Glu Tyr Ser Met Arg Leu Asp
                165                 170                 175

Asp Trp Val Leu Cys Arg Ile Tyr Lys Lys Ser His Ala Ser Leu Ser
            180                 185                 190

Ser Pro Asp Val Ala Leu Val Thr Ser Asn Gln Glu His Glu Glu Asn
        195                 200                 205

Asp Asn Glu Pro Phe Val Asp Arg Gly Thr Phe Leu Pro Asn Leu Gln
    210                 215                 220

Asn Asp Gln Pro Leu Lys Arg Gln Lys Ser Ser Cys Ser Phe Ser Asn
225                 230                 235                 240

Leu Leu Asp Ala Thr Asp Leu Thr Phe Leu Ala Asn Phe Leu Asn Glu
                245                 250                 255

Thr Pro Glu Asn Arg Ser Glu Ser Asp Phe Ser Phe Met Ile Gly Asn
            260                 265                 270

Phe Ser Asn Pro Asp Ile Tyr Gly Asn His Tyr Leu Asp Gln Lys Leu
        275                 280                 285

Pro Gln Leu Ser Ser Pro Thr Ser Glu Thr Ser Gly Ile Gly Ser Lys
    290                 295                 300

Arg Glu Arg Val Asp Phe Ala Glu Glu Thr Ile Asn Ala Ser Lys Lys
305                 310                 315                 320

Met Met Asn Thr Tyr Ser Tyr Asn Asn Ser Ile Asp Gln Met Asp His
                325                 330                 335

Ser Met Met Gln Gln Pro Ser Phe Leu Asn Gln Glu Leu Met Met Ser
            340                 345                 350

Ser His Leu Gln Tyr Gln Gly
        355

<210> SEQ ID NO 5
<211> LENGTH: 1035
<212> TYPE: DNA
<213> ORGANISM: Arabidopsis thaliana

<400> SEQUENCE: 5
atgattaaaa agttcagcaa tatggattac aaccagaaac gagagagatg tgggcaatac      60
atcgaagccc tcgaagagga acgtcgcaag attcatgtat tcaacgtga acttcctctt     120 tgcttagacc ttgtaactca agcgatcgag gcatgtaaga gggagttacc ggagatgacg     180
acggagaata tgtacggaca accagagtgc tcggagcaga cgaccggaga atgtgggccg     240
gtcttggagc agtttctaac tattaaagat tcatcgacat ccaacgaaga agaagatgaa     300
gaattcgacg atgagcatgg aaatcacgat ccagacaatg attccgagga caagaacacg     360
aaatctgatt ggcttaagtc tgttcaactc tggaatcaac ccgaccaccc acttcttcca     420
aaagaggaaa ggttgcagca ggagacgatg acaagagatg agagtatgag aaaagatccg     480
atggtgaacg gtggcgaagg gaggaagaga gaggcggaga agacggagg aggagggaga      540 aagcaaagaa ggtgttggtc gtcgcaattg catagacgct tcttgaacgc tcttcaacac     600
ttaggtggac ctcatgtagc tacgccaaag caatcaggg agtttatgaa ggttgatggg      660
ttaaccaatg atgaagttaa aagccattta cagaaatata gactgcatac aagaaggcca     720
```

```
cgccaaacag tccctaacaa cggaaactct caaacgcaac atttcgtagt cgtcggtggt    780
ttatgggtac cacaatcgga ctactctacg ggcaagacta ccggaggagc accaccagc    840 agtaccacca caaccaccgg catctatgga accatggccg caccgccacc tccacaatgg    900
cctagccatt ccaattatag accgtcgatt attgtggacg aaggatcggg aagtcatagt    960
gaaggggtcg tggtccggtg tagctcgccg gcgatgtctt cttctacccg taatcattac   1020
gtcaagaata attaa                                                    1035
```

<210> SEQ ID NO 6
<211> LENGTH: 344
<212> TYPE: PRT
<213> ORGANISM: Arabidopsis thaliana

<400> SEQUENCE: 6

```
Met Ile Lys Lys Phe Ser Asn Met Asp Tyr Asn Gln Lys Arg Glu Arg
1               5                  10                  15

Cys Gly Gln Tyr Ile Glu Ala Leu Glu Glu Arg Arg Lys Ile His
            20                  25                  30

Val Phe Gln Arg Glu Leu Pro Leu Cys Leu Asp Leu Val Thr Gln Ala
        35                  40                  45

Ile Glu Ala Cys Lys Arg Glu Leu Pro Glu Met Thr Thr Glu Asn Met
    50                  55                  60

Tyr Gly Gln Pro Glu Cys Ser Glu Gln Thr Thr Gly Glu Cys Gly Pro
65                  70                  75                  80

Val Leu Glu Gln Phe Leu Thr Ile Lys Asp Ser Ser Thr Ser Asn Glu
                85                  90                  95

Glu Glu Asp Glu Glu Phe Asp Asp Glu His Gly Asn His Asp Pro Asp
            100                 105                 110

Asn Asp Ser Glu Asp Lys Asn Thr Lys Ser Asp Trp Leu Lys Ser Val
        115                 120                 125

Gln Leu Trp Asn Gln Pro Asp His Pro Leu Leu Pro Lys Glu Glu Arg
    130                 135                 140

Leu Gln Gln Glu Thr Met Thr Arg Asp Glu Ser Met Arg Lys Asp Pro
145                 150                 155                 160

Met Val Asn Gly Gly Glu Gly Arg Lys Arg Glu Ala Glu Lys Asp Gly
                165                 170                 175

Gly Gly Gly Arg Lys Gln Arg Arg Cys Trp Ser Ser Gln Leu His Arg
            180                 185                 190

Arg Phe Leu Asn Ala Leu Gln His Leu Gly Gly Pro His Val Ala Thr
        195                 200                 205

Pro Lys Gln Ile Arg Glu Phe Met Lys Val Asp Gly Leu Thr Asn Asp
    210                 215                 220

Glu Val Lys Ser His Leu Gln Lys Tyr Arg Leu His Thr Arg Arg Pro
225                 230                 235                 240

Arg Gln Thr Val Pro Asn Asn Gly Asn Ser Gln Thr Gln His Phe Val
                245                 250                 255

Val Val Gly Gly Leu Trp Val Pro Gln Ser Asp Tyr Ser Thr Gly Lys
            260                 265                 270

Thr Thr Gly Gly Ala Thr Thr Ser Ser Thr Thr Thr Thr Gly Ile
        275                 280                 285

Tyr Gly Thr Met Ala Ala Pro Pro Pro Gln Trp Pro Ser His Ser
    290                 295                 300

Asn Tyr Arg Pro Ser Ile Ile Val Asp Glu Gly Ser Gly Ser His Ser
```

```
                305                 310                 315                 320
Glu Gly Val Val Arg Cys Ser Ser Pro Ala Met Ser Ser Thr
                    325                 330                 335

Arg Asn His Tyr Val Lys Asn Asn
                340

<210> SEQ ID NO 7
<211> LENGTH: 717
<212> TYPE: DNA
<213> ORGANISM: Arabidopsis thaliana

<400> SEQUENCE: 7
atggcacttg aaactcttac ttctccaaga ttatcttctc cgatgccgac tctgtttcaa      60
gattcagcac tagggtttca tggaagcaaa ggcaaacgat ctaagcgatc aagatctgaa     120
ttcgaccgtc agagtctcac ggaggatgaa tatatcgctt tatgtctcat gcttcttgct     180
cgcgacggag atagaaaccg tgaccttgac ctgccttctt cttcgtcttc acctcctctg     240
cttcctcctc ttcctactcc gatctacaag tgtagcgtct gtgacaaggc gttttcgtct     300
taccaggctc ttggtggaca caaggcaagt caccggaaaa gcttttcgct tactcaatct     360
gccgaggaga tgagctgtc gacatcgtcg gcgataacca cgtctggtat atccggtggc     420
gggggaggaa gtgtgaagtc gcacgtttgc tctatctgtc ataaatcgtt cgccaccggt     480
caagctctcg gcggccacaa acggtgccac tacgaaggaa agaacggagg cggtgtgagt     540
agtagcgtgt cgaattctga agatgtgggg tctacaagcc acgtcagcag tggccaccgt     600
gggtttgacc tcaacatacc gccgataccg aattctcga tggtcaacgg agacgaagag      660
gtgatgagtc ctatgccggc gaagaaactc cggtttgact tcccggagaa accctaa       717

<210> SEQ ID NO 8
<211> LENGTH: 238
<212> TYPE: PRT
<213> ORGANISM: Arabidopsis thaliana

<400> SEQUENCE: 8

Met Ala Leu Glu Thr Leu Thr Ser Pro Arg Leu Ser Ser Pro Met Pro
1               5                   10                  15

Thr Leu Phe Gln Asp Ser Ala Leu Gly Phe His Gly Ser Lys Gly Lys
            20                  25                  30

Arg Ser Lys Arg Ser Arg Ser Glu Phe Asp Arg Gln Ser Leu Thr Glu
        35                  40                  45

Asp Glu Tyr Ile Ala Leu Cys Leu Met Leu Leu Ala Arg Asp Gly Asp
    50                  55                  60

Arg Asn Arg Asp Leu Asp Leu Pro Ser Ser Ser Ser Pro Pro Leu
65                  70                  75                  80

Leu Pro Pro Leu Pro Thr Pro Ile Tyr Lys Cys Ser Val Cys Asp Lys
                85                  90                  95

Ala Phe Ser Ser Tyr Gln Ala Leu Gly Gly His Lys Ala Ser His Arg
            100                 105                 110

Lys Ser Phe Ser Leu Thr Gln Ser Ala Gly Gly Asp Glu Leu Ser Thr
        115                 120                 125

Ser Ser Ala Ile Thr Thr Ser Gly Ile Ser Gly Gly Gly Gly Ser
    130                 135                 140

Val Lys Ser His Val Cys Ser Ile Cys His Lys Ser Phe Ala Thr Gly
145                 150                 155                 160

Gln Ala Leu Gly Gly His Lys Arg Cys His Tyr Glu Gly Lys Asn Gly
```

```
              165                 170                 175
Gly Gly Val Ser Ser Val Ser Asn Ser Glu Asp Val Gly Ser Thr
            180                 185                 190

Ser His Val Ser Ser Gly His Arg Gly Phe Asp Leu Asn Ile Pro Pro
        195                 200                 205

Ile Pro Glu Phe Ser Met Val Asn Gly Asp Glu Val Met Ser Pro
    210                 215                 220

Met Pro Ala Lys Lys Leu Arg Phe Asp Phe Pro Glu Lys Pro
225                 230                 235

<210> SEQ ID NO 9
<211> LENGTH: 903
<212> TYPE: DNA
<213> ORGANISM: Arabidopsis thaliana

<400> SEQUENCE: 9
atggcgactc ctaacgaagt atctgcactt tggttcatcg agaaacatct actcgacgag      60
gcttctcctg tggctacaga tccatggatg aagcacgaat catcatcagc aacagaatct     120
agctctgact cttcttctat catcttcgga tcatcgtcct cttctttcgc cccaattgat     180
ttctctgaat ccgtatgcaa acctgaaatc atcgatctcg atactcccag atctatggaa     240
tttctatcga ttccatttga atttgactca gaagtttctg tttctgattt cgattttaaa     300
ccttctaatc aaaatcaaaa tcagtttgaa ccggagctta atctcaaat cgtaaaccg      360 ccattgaaga tttcgcttcc agctaaaaca gagtggattc aattcgcagc tgaaaacacc     420
aaaccggaag ttactaaacc ggtttcgaa gaagagaaga agcattacag aggagtaaga     480
caaagaccgt gggggaaatt cgcggcggag attcgtgacc cgaataaacg cggatctcgc     540
gtttggcttg gacgtttga tacagcgatt gaagcggcta gagcttatga cgaagcagcg     600
tttagactac gaggatcgaa agcgattttg aatttccctc ttgaagttgg aagtggaaa      660 ccacgcgccg atgaaggtga aagaaaacgg aagagacg atgatgagaa agtgactgtg      720
gttgagaaag tgttgaagac ggaacagagc gttgacgtta acggtggaga gacgttccg      780 tttgtaacgt cgaatttaac ggaattatgt gactgggatt taacgggggtt tcttaacttt     840 ccgcttctgt cgccgttatc tcctcatcca ccgtttggtt attcccagtt gaccgttgtt     900
tga                                                                     903

<210> SEQ ID NO 10
<211> LENGTH: 300
<212> TYPE: PRT
<213> ORGANISM: Arabidopsis thaliana

<400> SEQUENCE: 10

Met Ala Thr Pro Asn Glu Val Ser Ala Leu Trp Phe Ile Glu Lys His
1               5                   10                  15

Leu Leu Asp Glu Ala Ser Pro Val Ala Thr Asp Pro Trp Met Lys His
            20                  25                  30

Glu Ser Ser Ser Ala Thr Glu Ser Ser Asp Ser Ser Ser Ile Ile
        35                  40                  45

Phe Gly Ser Ser Ser Ser Phe Ala Pro Ile Asp Phe Ser Glu Ser
    50                  55                  60

Val Cys Lys Pro Glu Ile Ile Asp Leu Asp Thr Pro Arg Ser Met Glu
65                  70                  75                  80

Phe Leu Ser Ile Pro Phe Glu Phe Asp Ser Glu Val Ser Val Ser Asp
                85                  90                  95
```

```
Phe Asp Phe Lys Pro Ser Asn Gln Asn Gln Phe Glu Pro Glu
            100                 105                 110

Leu Lys Ser Gln Ile Arg Lys Pro Leu Lys Ile Ser Leu Pro Ala
        115                 120                 125

Lys Thr Glu Trp Ile Gln Phe Ala Ala Glu Asn Thr Lys Pro Glu Val
130                 135                 140

Thr Lys Pro Val Ser Glu Glu Lys Lys His Tyr Arg Gly Val Arg
145                 150                 155                 160

Gln Arg Pro Trp Gly Lys Phe Ala Ala Glu Ile Arg Asp Pro Asn Lys
                165                 170                 175

Arg Gly Ser Arg Val Trp Leu Gly Thr Phe Asp Thr Ala Ile Glu Ala
            180                 185                 190

Ala Arg Ala Tyr Asp Glu Ala Ala Phe Arg Leu Arg Gly Ser Lys Ala
        195                 200                 205

Ile Leu Asn Phe Pro Leu Glu Val Gly Lys Trp Lys Pro Arg Ala Asp
    210                 215                 220

Glu Gly Glu Lys Lys Arg Lys Arg Asp Asp Glu Lys Val Thr Val
225                 230                 235                 240

Val Glu Lys Val Leu Lys Thr Glu Gln Ser Val Asp Val Asn Gly Gly
                245                 250                 255

Glu Thr Phe Pro Phe Val Thr Ser Asn Leu Thr Glu Leu Cys Asp Trp
            260                 265                 270

Asp Leu Thr Gly Phe Leu Asn Phe Pro Leu Leu Ser Pro Leu Ser Pro
        275                 280                 285

His Pro Pro Phe Gly Tyr Ser Gln Leu Thr Val Val
    290                 295                 300

<210> SEQ ID NO 11
<211> LENGTH: 30
<212> TYPE: DNA
<213> ORGANISM: Artificial Sequence
<220> FEATURE:
<223> OTHER INFORMATION: Synthetic

<400> SEQUENCE: 11
gatggcaagg tcaccttgtt gcgagaagaa                                     30

<210> SEQ ID NO 12
<211> LENGTH: 30
<212> TYPE: DNA
<213> ORGANISM: Artificial Sequence
<220> FEATURE:
<223> OTHER INFORMATION: Synthetic

<400> SEQUENCE: 12
tataataaaa ccattaacgt ccaagaaatc                                     30

<210> SEQ ID NO 13
<211> LENGTH: 30
<212> TYPE: DNA
<213> ORGANISM: Artificial Sequence
<220> FEATURE:
<223> OTHER INFORMATION: Synthetic

<400> SEQUENCE: 13
gatgataagc aaggatccaa gatcgagttt                                     30

<210> SEQ ID NO 14
<211> LENGTH: 30
```

<212> TYPE: DNA
<213> ORGANISM: Artificial Sequence
<220> FEATURE:
<223> OTHER INFORMATION: Synthetic

<400> SEQUENCE: 14
gccttgatat tgaaggtgag aactcatcat                                30

<210> SEQ ID NO 15
<211> LENGTH: 30
<212> TYPE: DNA
<213> ORGANISM: Artificial Sequence
<220> FEATURE:
<223> OTHER INFORMATION: Synthetic

<400> SEQUENCE: 15
gatgattaaa aagttcagca atatggatta                                30

<210> SEQ ID NO 16
<211> LENGTH: 30
<212> TYPE: DNA
<213> ORGANISM: Artificial Sequence
<220> FEATURE:
<223> OTHER INFORMATION: Synthetic

<400> SEQUENCE: 16
attattcttg acgtaatgat tacgggtaga                                30

<210> SEQ ID NO 17
<211> LENGTH: 30
<212> TYPE: DNA
<213> ORGANISM: Artificial Sequence
<220> FEATURE:
<223> OTHER INFORMATION: Synthetic

<400> SEQUENCE: 17
gatggcactt gaaactctta cttctccaag                                30

<210> SEQ ID NO 18
<211> LENGTH: 30
<212> TYPE: DNA
<213> ORGANISM: Artificial Sequence
<220> FEATURE:
<223> OTHER INFORMATION: Synthetic

<400> SEQUENCE: 18
gggtttctcc gggaagtcaa accggagttt                                30

<210> SEQ ID NO 19
<211> LENGTH: 30
<212> TYPE: DNA
<213> ORGANISM: Artificial Sequence
<220> FEATURE:
<223> OTHER INFORMATION: Synthetic

<400> SEQUENCE: 19
gatggcgact cctaacgaag tatctgcact                                30

<210> SEQ ID NO 20
<211> LENGTH: 32
<212> TYPE: DNA
<213> ORGANISM: Artificial Sequence
<220> FEATURE:
<223> OTHER INFORMATION: Synthetic

<400> SEQUENCE: 20

-continued

```
aacaacggtc aactgggaat aaccaaacgg tg                                        32
```

<210> SEQ ID NO 21
<211> LENGTH: 12
<212> TYPE: PRT
<213> ORGANISM: Arabidopsis thaliana

<400> SEQUENCE: 21

Leu Asp Leu Asp Leu Glu Leu Arg Leu Gly Phe Ala
1               5                   10

<210> SEQ ID NO 22
<211> LENGTH: 23
<212> TYPE: DNA
<213> ORGANISM: Artificial Sequence
<220> FEATURE:
<223> OTHER INFORMATION: Synthetic

<400> SEQUENCE: 22

```
gaagttcatt tcatttggag agg                                                  23
```

<210> SEQ ID NO 23
<211> LENGTH: 22
<212> TYPE: DNA
<213> ORGANISM: Artificial Sequence
<220> FEATURE:
<223> OTHER INFORMATION: Synthetic

<400> SEQUENCE: 23

```
agaccggcaa caggattcaa tc                                                   22
```

<210> SEQ ID NO 24
<211> LENGTH: 6
<212> TYPE: PRT
<213> ORGANISM: Artificial sequence
<220> FEATURE:
<223> OTHER INFORMATION: synthetic
<220> FEATURE:
<221> NAME/KEY: MISC_FEATURE
<222> LOCATION: (4)..(4)
<223> OTHER INFORMATION: Asn or Glu
<220> FEATURE:
<221> NAME/KEY: MISC_FEATURE
<222> LOCATION: (6)..(6)
<223> OTHER INFORMATION: any amino acid

<400> SEQUENCE: 24

Leu Asp Leu Xaa Leu Xaa
1               5

<210> SEQ ID NO 25
<211> LENGTH: 5
<212> TYPE: PRT
<213> ORGANISM: Artificial sequence
<220> FEATURE:
<223> OTHER INFORMATION: synthetic
<220> FEATURE:
<221> NAME/KEY: MISC_FEATURE
<222> LOCATION: (5)..(5)
<223> OTHER INFORMATION: Phe or Ile

<400> SEQUENCE: 25

Phe Asp Leu Asn Xaa
1               5

<210> SEQ ID NO 26
<211> LENGTH: 6
<212> TYPE: PRT

```
<213> ORGANISM: Artificial sequence
<220> FEATURE:
<223> OTHER INFORMATION: synthetic
<220> FEATURE:
<221> NAME/KEY: misc_feature
<222> LOCATION: (3)..(3)
<223> OTHER INFORMATION: Glu, Gln or Asp

<400> SEQUENCE: 26

Asp Leu Xaa Leu Arg Leu
1               5

<210> SEQ ID NO 27
<211> LENGTH: 6
<212> TYPE: PRT
<213> ORGANISM: Artificial sequence
<220> FEATURE:
<223> OTHER INFORMATION: synthetic
<220> FEATURE:
<221> NAME/KEY: MISC_FEATURE
<222> LOCATION: (3)..(3)
<223> OTHER INFORMATION: Glu, Gln or Asp

<400> SEQUENCE: 27

Asp Leu Xaa Leu Arg Leu
1               5

<210> SEQ ID NO 28
<211> LENGTH: 6
<212> TYPE: PRT
<213> ORGANISM: Artificial sequence
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Asp, Asn, Glu, Gln, Thr or Ser
<220> FEATURE:
<221> NAME/KEY: MISC_FEATURE
<222> LOCATION: (3)..(3)
<223> OTHER INFORMATION: Asp, Gln, Asn, Arg, Glu, Thr, Ser or His
<220> FEATURE:
<221> NAME/KEY: MISC_FEATURE
<222> LOCATION: (5)..(5)
<223> OTHER INFORMATION: Arg, Gln, Asn, Thr, Ser, His, Lys or As

<400> SEQUENCE: 28

Xaa Leu Xaa Leu Xaa Leu
1               5

<210> SEQ ID NO 29
<211> LENGTH: 6
<212> TYPE: PRT
<213> ORGANISM: Artificial sequence
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Asp, Asn, Glu, Gln, Thr, or Ser
<220> FEATURE:
<221> NAME/KEY: MISC_FEATURE
<222> LOCATION: (3)..(3)
<223> OTHER INFORMATION: Asp, Gln, Asn, Arg, Glu, Thr, Ser, or His
<220> FEATURE:
<221> NAME/KEY: MISC_FEATURE
<222> LOCATION: (5)..(5)
<223> OTHER INFORMATION: Gln, Asn, Thr, Ser, His, Lys, or Asp

<400> SEQUENCE: 29

Xaa Leu Xaa Leu Xaa Leu
1               5
```

```
<210> SEQ ID NO 30
<211> LENGTH: 6
<212> TYPE: PRT
<213> ORGANISM: Artificial sequence
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Asp, Asn, Glu, Gln, Thr, or Ser
<220> FEATURE:
<221> NAME/KEY: MISC_FEATURE
<222> LOCATION: (3)..(3)
<223> OTHER INFORMATION: Asn, Arg, Thr, Ser, or His

<400> SEQUENCE: 30

Xaa Leu Xaa Leu Arg Leu
1               5

<210> SEQ ID NO 31
<211> LENGTH: 6
<212> TYPE: PRT
<213> ORGANISM: Artificial sequence
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Asn, Glu, Gln, Thr, or Ser
<220> FEATURE:
<221> NAME/KEY: MISC_FEATURE
<222> LOCATION: (3)..(3)
<223> OTHER INFORMATION: Asp, Gln, Asn, Arg, Glu, Thr, Ser, or His

<400> SEQUENCE: 31

Xaa Leu Xaa Leu Arg Leu
1               5

<210> SEQ ID NO 32
<211> LENGTH: 6
<212> TYPE: PRT
<213> ORGANISM: Artificial sequence
<220> FEATURE:
<223> OTHER INFORMATION: synthetic
<220> FEATURE:
<221> NAME/KEY: MISC_FEATURE
<222> LOCATION: (3)..(3)
<223> OTHER INFORMATION: Glu, Asp, or Gln

<400> SEQUENCE: 32

Asp Leu Xaa Leu Arg Leu
1               5
```

METHOD FOR PRODUCTION OF PLANT IMPARTED WITH STRESS TOLERANCE AND USE THEREOF

TECHNICAL FIELD

The present invention relates to a new technique for imparting a plant with a stress tolerance. To be more specific, the present invention relates to a method for production of a plant imparted with a salt tolerance and/or a high osmotic pressure tolerance and use thereof.

BACKGROUND ART

In view of the increase in food production and environment conservation, there has been expected production of plants having a tolerance against environmental stresses such as salt and an osmotic pressure. Researches on plants having a tolerance against environmental stresses have been made so far, and there have been reported isolation of plants having resistant mutation (see Non-patent Literatures 1 and 2 for example) and imparting of tolerance by overexpression (see Non-patent Literatures 3 and 4 for example).

CITATION LIST

Patent Literatures

Patent Literature 1: Japanese Patent Application Publication Tokukai No. 2001-269177 (published on Oct. 2, 2001)
Patent Literature 2: Japanese Patent Application Publication Tokukai No. 2001-269178 (published on Oct. 2, 2001)
Patent Literature 3: Japanese Patent Application Publication Tokukai No. 2001-292776 (published on Oct. 2, 2001)
Patent Literature 4: Japanese Patent Application Publication Tokukai No. 2001-292777 (published on Oct. 23, 2001)
Patent Literature 5: Japanese Patent Application Publication Tokukai No. 2001-269176 (published on Oct. 2, 2001)
Patent Literature 6: Japanese Patent Application Publication Tokukai No. 2001-269179 (published on Oct. 2, 2001)
Patent Literature 7: Japanese Patent Application Publication Tokukai No. 2005-13214 (published on Jan. 20, 2005)
Patent Literature 8: Japanese Patent Application Publication Tokukai No. 2005-27654 (published on Feb. 3, 2005)
Patent Literature 9: Japanese Patent Application Publication Tokukai No. 2005-204573 (published on Aug. 4, 2005)
Patent Literature 10: Japanese Patent Application Publication Tokukai No. 2006-006248 (published on Jan. 12, 2006)
Patent Literature 11: Japanese Patent Application Publication Tokukai No. 2006-020607 (published on Jan. 26, 2006)

Non-Patent Literatures

Non-patent Literature 1: The Plant Cell (1998) 10: 1181-91
Non-patent Literature 2: FEBS Lett. (2006) 580: 6537-42
Non-patent Literature 3: Nat. Biotechnol. (1999) 17: 287-91
Non-patent Literature 4: J. Biol. Chem. (2007) 282: 9260-8
Non-patent Literature 5: The Plant Cell (2001) 13: 1959-1968
Non-patent Literature 6: FEBS Letters (2002) 514: 351-354
Non-patent Literature 7: The Plant Cell (2007) 19: 473-484
Non-patent Literature 8: Plant Physiol. (2003) 132(3): 1415-23
Non-patent Literature 9: Plant Physiol. (2007) 145: 147-59
Non-patent Literature 10: The Plant Cell (2000) 12(3): 393-404

SUMMARY OF INVENTION

Technical Problem

However, most of the resistant mutations shown in Non-patent Literatures 1 and 2 are recessive traits, and so it is difficult to make practical use of plants having the resistant mutations. Further, imparting of tolerance by overexpression shown in Non-patent Literatures 3 and 4 may have an influence on growth of plants and forms of plants, and so it is difficult to make practical use of plants imparted with a tolerance by overexpression.

The present invention was made in view of the foregoing problems. An object of the present invention is to provide a technique of easily producing a plant imparted with a stress tolerance.

Solution to Problem

The inventors of the present invention have so far developed a technique of converting a transcription factor into a transcription inhibiting factor. This technique is useful for analyzing functions of various plant genes in vivo. In this technique, any gene is regarded as a target (target gene), for example, the effecter plasmid is introduced into plant cells so as to inhibit transcription of the target gene, resulting in inhibition of the function of the target gene in the plant to which the effecter plasmid has been introduced. Consequently, observing the phenotype expressed in the transgenic plant enables analysis of the function of the target gene. As for functional peptide usable in such a technique, see Patent Literatures 1-8 and Non-patent Literatures 5-6 etc. These documents are incorporated herein for reference.

The inventors of the present invention have used the above technique and found that a transcription factor family (TCP family) protein is essential for normal morphogenesis of a flower and inhibiting the function of this protein enables effectively changing the shape of the flower (see Patent Literatures 9-11 and Non-patent Literature 7). The inventors of the present invention have further studied in order to clarify TCP family-related signaling for morphogenesis of leaves and found various genes whose expressions increase by inhibiting the function of the TCP family protein.

The various genes whose expressions increase by inhibiting the function of the TCP family protein include a transcription factor whose function was unknown. The inventors of the present invention have further studied to find what role this transcription factor plays in morphogenesis of leaves, and found that this transcription factor is related to a function entirely different from morphogenesis of leaves. Thus, the present invention has been completed.

A method of the present invention for producing a plant with a stress tolerance includes the step of inhibiting, in a plant, a function of a first polypeptide including an amino acid sequence represented by any one of SEQ ID NOS: 2, 4, 6, 8, and 10.

As described above, the function of the first polypeptide had not been known other than the fact that the first polypeptide is a transcription factor. Further, the function conceivable from the study of TCP family proteins (control of morphogenesis of leaves) and a stress tolerance are not related to each other at all. Thus, a person skilled in the art did not know, and could not have expected, that the first polypeptide is related a stress tolerance.

It is preferable to arrange the method of the present invention such that the step of inhibiting a function of a first polypeptide is carried out in such a manner that a fusion protein of the first polypeptide and a second polypeptide which converts any transcription factor into a transcription inhibiting factor is produced in the plant.

The second polypeptide is a functional peptide which was developed by the inventors of the present invention, and has a function of converting any transcription factor into a transcription inhibiting factor. Since such a peptide can be used as a selection marker, it is possible to select a desired plant without using chemical agents. Further, most of resistant mutations isolated so far are recessive traits and it is not easy to make practical use of plants having such resistant mutations. On the other hand, use of the functional peptide enables imparting a resistant trait as a dominant trait, and also enables inducing the resistant trait by a specific promoter. Further, since the resistant trait serves as a dominant trait, the functional peptide is applicable to plants whose gene information is little known.

The method of the present invention may be arranged such that the step of inhibiting a function of a first polypeptide is carried out in such a manner that expression of the first polypeptide is inhibited in the plant. In this case, the inhibition of the expression of the first polypeptide may be made by a knock-put process or an RNAi process.

It is preferable to arrange the method of the present invention such that the stress tolerance is a salt tolerance and/or a high osmotic pressure tolerance.

The plant of the present invention is produced by the above method. It is preferable that the plant of the present invention is selected from the group consisting of a grown plant individual, a plant cell, a plant tissue, a callus, and a seed.

A kit of the present invention for producing a plant with a stress tolerance includes: a first polynucleotide including a base sequence represented by any one of SEQ ID NOS: 1, 3, 5, 7, and 9; and a second polynucleotide encoding a functional peptide which converts any transcription factor into a transcription inhibiting factor.

A kit of the present invention for producing a plant with a stress tolerance may include: an oligonucleotide set including any one of a first primer set (SEQ ID NOS: 11 and 12), a second primer set (SEQ ID NOS: 13 and 14), a third primer set (SEQ ID NOS: 15 and 16), a fourth primer set (SEQ ID NOS: 17 and 18), and a fifth primer set (SEQ ID NOS: 19 and 20); and a polynucleotide (second polynucleotide) encoding a functional peptide which converts any transcription factor into a transcription inhibiting factor.

It is preferable that the kit of the present invention further includes an expression vector for expressing a target polypeptide in a plant. It is more preferable that the kit of the present invention further includes reagents for introducing the expression vector into a plant cell.

The method of the present invention for producing a plant may be a method for imparting a plant with a stress tolerance. Further, the kit of the present invention may be a kit for imparting a plant with a stress tolerance.

Advantageous Effects of Invention

The present invention enables imparting a plant with a salt tolerance and an osmotic pressure tolerance. This enables producing a functional plant capable of standing up to salt damage or dryness. This enables producing a desired crop in a wide variety of areas.

DESCRIPTION OF EMBODIMENTS

Figure 1:
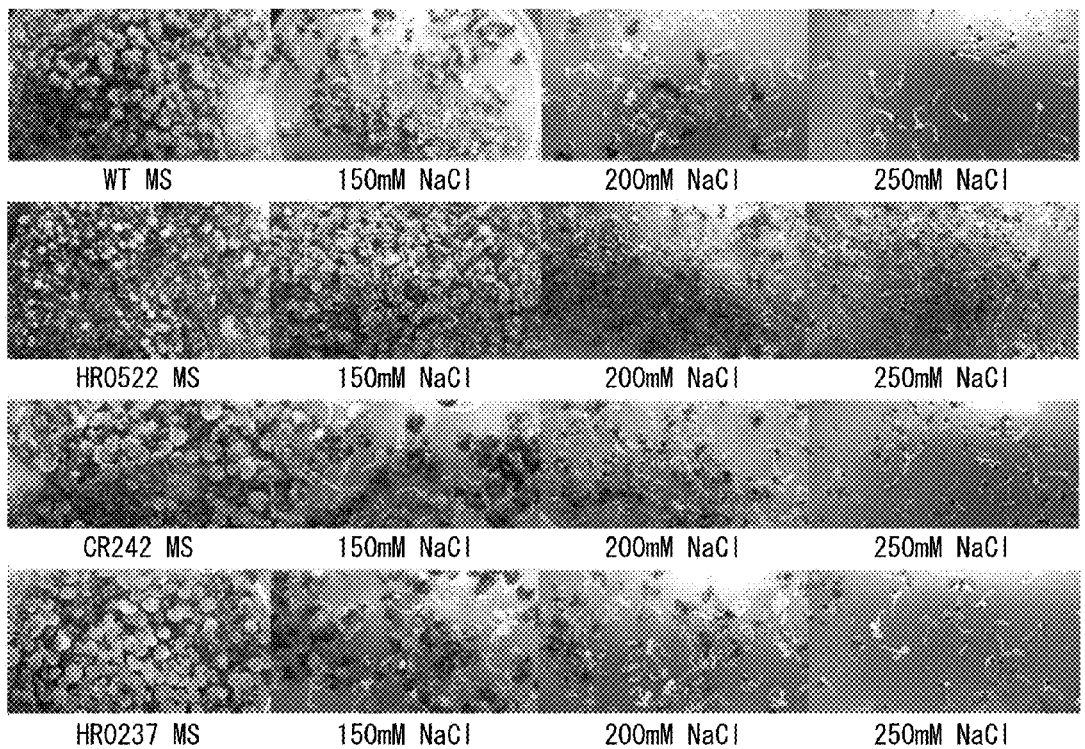
FIG. 1 shows states of wild type *Arabidopsis thaliana* and *Arabidopsis thaliana* expressing a salt-tolerance chimeric repressor, which were three weeks after sowing with various salt concentrations.

The present invention provides a method for production of a plant with a stress tolerance. The method of the present invention includes the step of inhibiting a function of a particular transcription factor in a plant.

In the present invention, "transcription factor (transcription factor etc.)" indicates a transcription factor or a DNA-binding domain of the transcription factor, and is preferably a transcription factor of a plant. "transcription factor" indicates a polypeptide (transcription control factor) which positively or negatively controls transcription or initiation reaction of the transcription, and is preferably a polypeptide which positively controls the transcription or initiation reaction of the transcription.

The term "polypeptide" used herein is compatible with "peptide" or "protein". The term "fragment" of polypeptide indicates a partial fragment of the polypeptide. The polypeptide according to the present invention may be isolated from a natural source or may be synthesized chemically.

The term "isolated" polypeptide or protein indicates polypeptide or protein extracted from its natural environment. For example, recombinantly produced polypeptide or protein expressed in a host cell is considered as being isolated, as with natural or recombinant polypeptide or protein which is substantially purified by any proper technique.

Examples of the "polypeptide" include naturally purified products, chemically synthesized products, and products produced by a recombinant technique from a prokaryote host or a eucaryote host (e.g. bacteria cells, yeast cells, higher plant cells, insect cells, and mammal cells). The "polypeptide" may be glycosylated or non-glycosylated depending on a host used in a recombinant production process. Further, in some cases, the "polypeptide" may contain a modified methionine residue resulting from a start codon as a result of a host-mediated expression process.

The "polypeptide" may be polypeptide in which amino acids are bound to each other by a peptide bond. Alternatively, the "polypeptide" may be a complex polypeptide including a structure other than polypeptide. Examples of the "structure other than polypeptide" used herein include, but not limited to, glycans and isoprenoid groups.

The term "polynucleotide" used herein is compatible with "gene", "nucleic acid", or "nucleic acid molecule", and indicates a polymer of nucleotides. The term "base sequence" used herein is compatible with "nucleic acid sequence" or "nucleotide sequence", and is shown as a sequence of deoxyribonucleotides (abbreviated as A, G, C, and T).

Polynucleotide can exist in the form of RNA (e.g. mRNA) or in the form of DNA (e.g. cDNA or genome DNA). DNA may be double-stranded or single-stranded. The single-stranded DNA or RNA may be a code strand (also known as a sense strand) or may be a non-code strand (also known as anti-sense strand).

The expression "inhibit the function of a transcription factor" indicates causing the function of the transcription factor as a transcription control factor to be lost. Examples of the loss of the transcription control factor include loss of an interactional function between proteins, loss of a DNA binding function, loss of a transcription control function and/or inversion of the transcription control function. A person skilled in the art who reads the present specification easily understands that a transcription factor having lost these functions is inhibited from realizing these functions. As described above, inhibiting the function of a transcription factor suppresses expression of a target gene which is a target of the transcription factor. Alternatively, inhibiting the function of a transcription factor suppresses expression of a downstream gene which is positioned downstream of the transcription factor, resulting in subdual of the function of the downstream gene. That is, in the present specification, the expression "inhibit the function of a transcription factor" is compatible with "suppress expression of a target gene which is a target of the transcription factor", "suppress expression of a downstream gene which is positioned downstream of the transcription factor", and "suppress the function of the downstream gene".

A method for inhibiting the function of a transcription factor may be inhibition of expression of a gene or protein corresponding to a target transcription factor in a plant, or may be inhibition of synthesis of RNA or inhibition of synthesis of protein. A method for inhibiting expression of protein may be a technique well known in the art. Examples of the technique include, but not limited to, a knock-out process and an RNAi process.

As described above, the inventors of the present invention have already developed a technique of converting a transcription factor into a transcription inhibiting factor. The "transcription inhibiting factor" used herein is compatible with "chimeric repressor", and is a fusion protein including a "transcription factor" and a "functional peptide". That is, in the present invention, in order to inhibit the function of a transcription factor, a fusion protein (chimeric repressor) of a target transcription factor and a functional peptide which converts any transcription factor into a transcription inhibiting factor may be expressed in a plant. In order to express a target protein in a plant, a gene encoding the protein is introduced into the plant. As described above, application of the chimeric repressor technique enables subduing expression of a target gene which is a target of a transcription factor. Alternatively, application of the chimeric repressor technique enables subduing expression of a downstream gene which is positioned downstream of the transcription factor, resulting in subdual of the function of the downstream gene.

In the present invention, the term "include" indicates substantially encompassing components, and may be replaced with "made of", but not limited to "consist of". That is, the term "made of" also indicates encompassing additional components.

The wording "a gene is introduced" used herein indicates that a gene is introduced into a target cell (host cell) by a well-known genetic engineering process (gene manipulation technique) in such a manner that the gene can be expressed in the target cell (i.e. transformant). Accordingly, the transformant used herein may be obtained by introducing a recombinant expression vector including a chimeric repressor gene into a living organism. Examples of the transformant used herein include not only cells but also tissues and organs of a living organism and individual plants or animals. The living organism is not particularly limited. Examples of a living organism to be used in the test include plants such as *Arabidopsis thaliana* and animals such as mice, rats, drosophilas, and nematodes.

Alternatively, in a case where the present invention is applied to an industrial field using plants, examples of the living organism include various products (plants and crops produced in agriculture, forestry and marine products industry). Specific examples of such products and crops include grains (e.g. rice plant, wheat, and corn), vegetables, flowers, ornamental plants, and timbers (e.g. pine, cedar, and Japanese cypress).

In the present specification, a method for introducing a gene into a plant is not particularly limited, but it is preferable that a target gene is incorporated into an expression vector. An example of the expression vector may be a publicly known plant transforming vector (e.g. binary vector (pBIN19, pBI121, pBIG etc.)). However, as described in Patent Literature 7, in a case where a publicly known plant transforming vector is used, some applications of the vector are unable to achieve a sufficient transformation ratio. Accordingly, it is preferable to use a vector for constructing an expression vector which is described in Patent Literature 7. A preferable expression vector is a vector which includes a promoter and a terminator for a plant and a target gene positioned between the promoter and the terminator and which expresses, in a host plant, a protein encoded by the target gene.

A method for transforming a plant by using such an expression vector is not particularly limited, and the recombinant expression vector may be introduced into a host by a suitable method of transformation according to the kind of the host. In the present invention, a particularly preferable example of the host is a plant. In this case, examples of the method for transformation are not particularly limited, and may be conventional and publicly known transformation such as transformation using a gene gun, protoplast/spheroplast transformation, *Agrobacterium* transformation, electroporation, calcium phosphate transformation, transformation using ribosome, and DEAE dextran transformation. In order to carry out the present invention, *Agrobacterium*-mediated transformation assisted by vacuum infiltration is preferable.

In order to confirm whether a target gene is introduced into a host cell or not and whether the target gene is surely expressed in the host cell or not, a marker may be used. For example, a gene which is deleted in the host cell is used as a marker, and a plasmid etc. including the marker and the target gene is introduced as an expression vector into the host cell. This enables confirmation of introduction of the target gene by observing expression of the marker gene. Alternatively, a target protein may be expressed as a fusion protein. For example, GFP (Green Fluorescent Protein) derived from *Aequorea victoria* is used as a marker and the target protein may be expressed as a GFP fusion protein. Alternatively, a gene for causing an expression site of a transgenic plant to be visible for monitoring may be introduced into a recombinant expression vector. An example of such a gene is β-glucuronidase (GUS) gene.

In the present specification, a transcription factor whose function is to be inhibited in order to impart a plant with a stress tolerance is also referred to as a first polypeptide. The first polypeptide is encoded by one of genes whose expression is increased by inhibiting the function of a TCP family protein known as relating to morphogenesis of a plant. As for the TCP family protein, see Patent Literatures 9-11 and Non-patent Literature 7. The first polypeptide is not related to the structure and the function of the TCP family protein.

In one embodiment, the first polypeptide may be a polypeptide made of an amino acid sequence represented by any one of SEQ ID. Nos. 2, 4, 6, 8, and 10, or may be a variant of the polypeptide which variant has the same function as that of the polypeptide. The function of the first polypeptide indicates a one inhibition of which enables imparting a plant with a stress tolerance. In the present invention, the stress tolerance is preferably a salt tolerance and/or a high osmotic pressure tolerance.

As described in later-mentioned Examples, the inventors of the present invention found that transcription factors At4g21440 (SEQ ID Nos. 1 and 2), At3g04070 (SEQ ID Nos. 3 and 4), and At1g13300 (SEQ ID Nos. 5 and 6) are related to a salt tolerance. That is, by inhibiting the function of the transcription factor At4g21440, At3g04070, or At1g13300, it is possible to prepare a plant with a salt tolerance. Further, the inventors of the present invention found that transcription factors At5g04340 (SEQ ID Nos. 7 and 8) and At5g47230 (SEQ ID Nos. 9 and 10) are related to a high osmotic pressure. That is, by inhibiting the function of the transcription factor At5g04340 or At5g47230, it is possible to prepare a plant with a high osmotic pressure tolerance.

It is reported that At4g21440 is "MYB102" which is involved in an injury and osmotic pressure stress signaling system (see Non-patent Literature 8). However, Non-patent Literature 8 neither describes nor suggests that inhibition of the function of At4g21440 in a plant enables imparting the plant with a salt tolerance. At3g04070 is also referred to as "ANAC047", but its function has not been reported. At1g13300 is considered as belonging to "GARP family", but its function has not been reported.

It is reported that At5g04340 is "ZAT6" which negatively controls growth of a main root of *Arabidopsis thaliana* and changes the structure of the root in order to balance phosphoric acid (see Non-patent Literature 9). However, Non-patent Literature 9 neither describes nor suggests that inhibition of the function of At5g04340 in a plant enables imparting the plant with a high osmotic pressure tolerance. It is reported that At5g47230 is "AtERF5" which is induced by injury (see Non-patent Literature 10). However, Non-patent Literature 10 neither describes nor suggests that inhibition of the function of At5g47230 in a plant enables imparting the plant with a high osmotic pressure tolerance.

In the present specification, an example of a variant is a polypeptide (protein) including an amino acid sequence derived from the amino acid sequence represented by any one of SEQ ID NOS: 2, 4, 6, and 10 by deletion, addition, or substitution of one or several amino acids. It is well known in the art that some amino acids in the amino acid sequence of the polypeptide can be easily modified without a significant influence on the structure or the function of the polypeptide. Further, it is also well known in the art that other than artificial modification, there exist variants of natural proteins in which structures or functions of the natural proteins are not significantly changed.

A person skilled in the art can easily mutate one or several amino acids in an amino acid sequence of a polypeptide by using a well-known art. For example, by employing publicly known point mutation, it is possible to mutate any base of a polynucleotide which encodes a polypeptide. Further, by designing a primer corresponding to any site of a polynucleotide which encodes a polypeptide, it is possible to prepare a variant with deletion or a variant with addition. Further, it is also possible to attain the object by using random variation.

In the present specification, another example of a variant is preferably a variant encoded by a polynucleotide including a base sequence derived from a base sequence represented by any one of SEQ ID Nos: 1, 3, 5, 7 and 9 by deletion, substitution, or addition of one or several bases.

In the present specification, another example of a variant is preferably a variant encoded by a polynucleotide which is hybridized, under a stringent condition, with a polynucleotide including a sequence complementary to a base sequence represented by any one of SEQ ID Nos: 1, 3, 5, 7 and 9.

Hybridization may be carried out by a well known method such as a method described in "Molecular Cloning: A Laboratory Manual, Third Edition, edited by J. Sambrook and D. W. Russell, Cold Spring Harbor Laboratory, NY (2001)" (incorporated herein for reference). Normally, higher temperature and lower salt concentration makes the condition more stringent (makes hybridization more difficult), so that a more homologous polynucleotide can be obtained. A temperature suitable for the hybridization varies according to a base sequence and the length of the base sequence. For example, in a case where a DNA fragment including eighteen bases encoding six amino acids is used as a probe, the temperature of 50° C. or less is preferable.

The term "stringent hybridization condition" used herein indicates one-night incubation at 42° C. in a hybridization solution (containing 50% formaldehyde, 5×SSC (150 mM NaCl and 15 mM trisodium citrate), 50 mM sodium phosphate (pH 7.6), 5×Denhardt's solution, 10% dextran sulfate, and 20 μg/ml denatured sonicated sermon sperm DNA), and then washing a filter at approximately 65° C. in 0.1×SSC.

In the present specification, "functional peptide" indicates a peptide capable of converting a transcription factor into a transcription inhibiting factor, and is compatible with "transcription inhibition converting peptide" or "repressor domain". In the present specification, the "functional peptide" is also referred to as a second polypeptide.

As described above, the "functional peptide" has been already well known in the art (see Patent Literatures 1-8 and Non-patent Literatures 5-6 etc.). Accordingly, a person skilled in the art can easily prepare a desired functional peptide by using a well-known technique such as a recombinant technique or chemical synthesis. Further, a person skilled in the art can easily prepare a fusion protein of a desired transcription factor and a desired functional peptide.

In one embodiment, it is preferable that the functional peptide includes an amino acid sequence represented by any one of

```
                                        (SEQ ID NO: 24)
(1) X1-Leu-Asp-Leu-X2-Leu-X3

(SEQ ID NO: 25)
(2) Y1-Phe-Asp-Leu-Asn-Y2-Y3

(SEQ ID NO: 26)
(3) Z1-Asp-Leu-Z2-Leu-Arg-Leu-Z3

(SEQ ID NO: 27)
(4) Asp-Leu-Z4-Leu-Arg-Leu
``` where X1 indicates 0-10 amino acid residues, X2 indicates Asn or Glu, X3 indicates at least 6 amino acid residues, Y1 indicates 0-10 amino acid residues, Y2 indicates Phe or Ile, Y3 indicates at least 6 amino acid residues, Z1 indicates Leu, Asp-Leu or Leu-Asp-Leu, Z2 indicates Glu, Gln, or Asp, Z3 indicates 0-10 amino acid residues, and Z4 indicates Glu, Gln, or Asp.

In the functional peptide represented by formula (1), the number of amino acid residues represented by X1 should be 0-10. The specific kind of an amino acid constituting the amino acid residue represented by X1 is not particularly limited. In other words, to an N-terminus of the functional peptide represented by formula (1), an oligomer made of any one amino acid or any two-ten amino acid residues may be added, or no amino acid may be added.

The amino acid residue represented by X1 should be as short as possible in consideration of easiness in synthesizing the functional peptide represented by formula (1). Specifically, the number of amino acid residues represented by X1 is preferably 10 or less, and more preferably 5 or less.

Similarly, in the functional peptide represented by formula (1), the number of amino acid residues represented by X3 should be at least 6. The specific kind of an amino acid sequence constituting the amino acid residue represented by X3 is not particularly limited. In other words, to a C-terminus of the functional peptide represented by formula (1), an oligomer made of any at least 6 amino acid residues should be added. The amino acid residues represented by X3 can express the above function provided that there exist at least 6 such amino acid residues.

In the functional peptide represented by formula (2), the number of amino acid residues represented by Y1 should be 0-10, as in the case of X1 in the functional peptide represented by formula (1). The specific kind of an amino acid constituting the amino acid residue represented by Y1 is not particularly limited. In other words, to an N-terminus of the functional peptide represented by formula (2), an oligomer made of any one amino acid or any two-ten amino acid residues may be added, or no amino acid may be added, as in the case of the functional peptide represented by formula (1).

The amino acid residue represented by Y1 should be as short as possible in consideration of easiness in synthesizing the functional peptide represented by formula (2). Specifically, the number of amino acid residues represented by Y1 is preferably 10 or less, and more preferably 5 or less.

Similarly, in the functional peptide represented by formula (2), the number of amino acid residues represented by Y3 should be at least 6, as in the case of X3 in the functional peptide represented by formula (1). The specific kind of an amino acid sequence constituting the amino acid residue represented by Y3 is not particularly limited. In other words, to a C-terminus of the functional peptide represented by formula (2), an oligomer made of any at least 6 amino acid residues should be added, as in the case of the functional peptide represented by formula (1). The amino acid residues represented by Y3 can exert the above function provided that there exist at least 6 such amino acid residues.

In the functional peptide represented by formula (3), the amino acid residue represented by Z1 includes Leu in the number of 1-3. In a case of one amino acid, the amino acid residue represented by Z1 includes Leu. In a case of two amino acids, Asp-Leu. In a case of three amino acids, Leu-Asp-Leu.

On the other hand, in the functional peptide represented by formula (3), the number of amino acid residues represented by Z3 should be 0-10, as in the case of X1 in the functional peptide represented by formula (1). The specific kind of an amino acid constituting the amino acid residue represented by Z3 is not particularly limited. In other words, to a C-terminus of the functional peptide represented by formula (3), an oligomer made of any one amino acid or any two-ten amino acid residues may be added, or no amino acid may be added.

The amino acid residue represented by Z3 should be as short as possible in consideration of easiness in synthesizing the functional peptide represented by formula (3). Specifically, the number of amino acid residues represented by Z3 is preferably 10 or less, and more preferably 5 or less. Specific examples of the amino acid residue represented by Z3 include, but not limited to, Gly, Gly-Phe-Phe, Gly-Phe-Ala, Gly-Tyr-Tyr, Ala-Ala-Ala.

The number of amino acid residues in the whole functional peptide represented by formula (3) is not particularly limited. However, in consideration of easiness in synthesis, the number is preferably 20 or less. The most preferable example of the functional peptide represented by formula (3) is peptide SRDX (LDLDLELRLGFA: SEQ ID NO: 21).

In another embodiment, it is preferable that the functional peptide includes an amino acid sequence represented by (SEQ ID NO: 28)
(5) α1-Leu-β1-Leu-γ1-Leu where α1 represents Asp, Asn, Glu, Gln, Thr, or Ser, β1 represents Asp, Gln, Asn, Arg, Glu, Thr, Ser, or His, and γ1 represents Arg, Gln, Asn, Thr, Ser, His, Lys, or Asp.

The amino acid sequence represented by formula (5) may be further classified into the following (6)-(9):

(SEQ ID NO: 29)
(6) α1-Leu-β1-Leu-γ2-Leu;

(SEQ ID NO: 30)
(7) α1-Leu-β2-Leu-Arg-Leu;
or (SEQ ID NO: 31)
(8) α2-Leu-β1-Leu-Arg-Leu (SEQ ID NO: 32)
(9) Asp-Leu-β3-Leu-Arg-Leu where α1 represents Asp, Asn, Glu, Gln, Thr, or Ser, α2 represents Asn, Glu, Gln, Thr, or Ser, β1 represents Asp, Gln, Asn, Arg, Glu, Thr, Ser, or His, β2 represents Asn, Arg, Thr, Ser, or His, β3 represents Glu, Asp, or Gln, and γ2 represents Gln, Asn, Thr, Ser, His, Lys, or Asp.

where α1 represents Asp, Asn, Glu, Gln, Thr, or Ser, α2 represents Asn, Glu, Gln, Thr, or Ser, β1 represents Asp, Gln, Asn, Arg, Glu, Thr, Ser, or His, β2 represents Asn, Arg, Thr, Ser, or His, β3 represents Glu, Asp, or Gln, and γ2 represents Gln, Asn, Thr, Ser, His, Lys, or Asp.

The functional peptide can convert any transcription factor into a transcription inhibiting factor by fusing with the transcription factor. Accordingly, by using an expression vector including a gene encoding a transcription factor etc. capable of binding to an expression control region of a specific target gene, it is possible to efficiently analyze the function of a plant gene in vivo.

In the present specification, the term "target gene" indicates any gene which is a target of a transcription factor etc. to be fused with a functional peptide. By introducing, to a plant, an expression vector including a chimera gene of a functional peptide and a transcription factor etc. in accordance with the present invention, a chimera protein derived from the chimera gene serves as a transcription inhibiting factor which inhibits transcription of the target gene in vivo. Consequently, a protein encoded by the target gene is not expressed.

As described above, the functional peptide can convert any transcription factor into a transcription inhibiting factor. Accordingly, by incorporating a transcription factor etc. which controls transcription of a specific target gene, it is possible to inhibit transcription of the target gene. Consequently, if a plant shows any change, it is possible to analyze the function of the target gene in consideration of the change.

The functional peptide can inhibit expression of a target gene in preference to activity of other transcription factor which is functionally redundant. Accordingly, if a transcription inhibition converting polynucleotide is incorporated into a constructing vector of the present invention, the constructing vector can be used for analyzing the function of the activity of the functionally redundant transcription factor.

For example, as a transcription factor for controlling formation of an apical bud of seedling, CUC1 protein and CUC2 protein are known. It is known that only when both of CUC1 gene and CUC2 gene respectively encoding these proteins have mutation, seed leaves of a plant having the CUC1 and CUC2 genes have a cup shape, and a meristem of an apical bud is not formed.

Even when only one of these functionally redundant genes (e.g. only CUC1 gene) is bound to the functional peptide to make a chimera gene and the chimera gene is expressed in a plant, an expressed chimera protein inhibits not only the transcription activity of the CUC1 protein but also the transcription activity of the CUC2 protein.

It is often that a plant has a plurality of transcription factors which are functionally redundant. Since a transcription inhibiting factor obtained by transforming the function of a transcription factor by the functional peptide is dominant, use of the present invention enables analysis of the function of a transcription factor which function has not been clarified by knocking out one gene. Further, the present invention is applicable to a plant having an amphidiploid genome, such as wheat.

A polynucleotide encoding the first polypeptide (herein, this polynucleotide is also referred to as a first polynucleotide) is not particularly limited as long as the polynucleotide contains a base sequence corresponding to an amino acid sequence of the first polypeptide, based on a genetic code. If necessary, the first polynucleotide may contain a base sequence serving as a connection site to be connected with a polynucleotide encoding a functional peptide (herein, this polynucleotide is also referred to as a second polynucleotide). Further, if the reading frame of the first polynucleotide does not correspond to the reading frame of the second polynucleotide, the first polynucleotide may contain an additional base sequence used to make these reading frames correspond to each other. Further, the first polynucleotide may be fused, at its 5' terminus or 3' terminus, with a polynucleotide encoding a tag marker (tag sequence or marker sequence).

Similarly, the second polynucleotide is not particularly limited as long as the second polynucleotide contains a base sequence corresponding to an amino acid sequence of the second polypeptide, based on a genetic code. If necessary, the second polynucleotide may contain a base sequence serving as a connection site to be connected with the first polynucleotide. Further, if the reading frame of the first polynucleotide does not correspond to the reading frame of the second polynucleotide, the second polynucleotide may contain an additional base sequence used to make these reading frames correspond to each other. Further, the second polynucleotide may be fused, at its 5' terminus or 3' terminus, with a polynucleotide encoding a tag marker (tag sequence or marker sequence).

In the present specification, the "gene encoding a transcription inhibiting factor which is a fusion protein of a transcription factor and a functional peptide" should be designed such that the first polynucleotide and the second polynucleotide are bound to each other in frame. Accordingly, the "first polynucleotide" and the "second polynucleotide" may be individually inserted into an expression vector to be used, or the "first polynucleotide" and the "second polynucleotide" may be bound to each other in advance and then simultaneously inserted into the expression vector. Further, an expression vector to which the second polynucleotide is inserted may be designed to have a "site to which the first polynucleotide is to be inserted" and a desired gene is inserted into the site.

A person skilled in the art who reads the present specification easily understands that the method of the present invention for production of a plant may be a method for imparting a plant with a stress tolerance. That is, the present invention provides a method for imparting a plant with a stress tolerance. The method includes the step of inhibiting the function of a transcription factor for controlling expression of the useful trait. In order to inhibit the function of the transcription factor, expression of the transcription factor may be inhibited in the plant, or a fusion protein (chimeric repressor) of the transcription factor and a functional peptide which converts any transcription factor into a transcription inhibiting factor may be expressed in the plant. The method for inhibiting expression of a protein should be a technique well known in the art. Examples thereof include, but not limited to, a knock-out process and an RNAi process.

Further, the present invention provides a kit for production of a plant with a stress tolerance. The kit of the present invention includes members necessary for carrying out the above method for production of a plant. In one embodiment, the kit includes at least a gene encoding a transcription factor (first polynucleotide) and a gene encoding a functional peptide (second polynucleotide). The kit in accordance with the present embodiment may include a fusion gene obtained by fusing these genes, and preferably, further include an expression vector for expressing a target polypeptide in a plant (plant transforming vector). In one aspect, the kit in accordance with the present embodiment includes a first polynucleotide including a base sequence represented by any one of SEQ ID Nos. 1, 3, 5, 7, and 9, and a second polynucleotide encoding a functional peptide for converting any transcription factor into a transcription inhibiting factor.

In another embodiment, the kit of the present invention may include, instead of the first polynucleotide, an oligonucleotide set necessary for obtaining the first polynucleotide. In order to produce a plant with a stress tolerance, the kit in accordance with the present embodiment includes a first primer pair (SEQ ID Nos. 11 and 12), a second primer pair (SEQ ID Nos. 13 and 14), a third primer pair (SEQ ID Nos. 15 and 16), a fourth primer pair (SEQ ID Nos. 17 and 18), or a fifth primer pair (SEQ ID Nos. 19 and 20), and a second polynucleotide encoding a functional peptide which converts any transcription factor into a transcription inhibiting factor. The kit in accordance with the present embodiment may further include reagents necessary for PCR.

The "kit" used herein indicates a member in which a plurality of components are packaged. For example, the kit indicates a member in which a "gene encoding a transcription factor", a "gene encoding a functional peptide", and a "plant transforming vector" in respective vessels are packaged. It is preferable that the kit of the present invention further includes reagents for introducing the expression vector into a plant cell.

A person skilled in the art who reads the present specification easily understands that reagents other than the reagents for the aforementioned polynucleotide or oligonucleotide may be ones publicly known in the art. Further, a person skilled in the art who reads the present specification easily understands that the kit for production of a plant with a stress tolerance may be used as a kit for imparting a plant with a stress tolerance.

Further, a person skilled in the art who reads the present specification easily understands that a plant produced by the method and the kit for production of a plant with a stress tolerance and a plant produced by the method and the kit for imparting a plant with a stress tolerance are also encompassed in the scope of the present invention.

EXAMPLES

1. Preparation of DNA Construct

Primers for amplifying protein-encoding regions of genes encoding transcription factors were synthesized (SEQ ID Nos. 11-20). PCR consisting of 25 cycles each having denaturation at 94° C. for 1 min, annealing at 47° C. for 2 min, and extension at 74° C. for 1 min was carried out. DNA fragments amplified by the PCR were inserted into SmaI sites of p35SSRDXG. p35SSRDXG is a vector having two recombinant sites derived from publicly known λ phage (hereinafter referred to as att site) and has cauliflower mosaic virus 35S promoter (hereinafter referred to as CaMV35S promoter), transcription inhibiting peptide SRDX derived from *Arabidopsis thaliana* (LDLDLELRLGFA: SEQ ID No. 21), and a transcription termination region of a gene of a nopaline synthesizing enzyme (hereinafter referred to as NOS-ter). Using the construct thus obtained, *Escherichia coli* was transformed. *Escherichia coli* thus transformed was proliferated and then the construct was prepared from the *Escherichia coli* and a base sequence of the construct was determined. A clone to which a gene encoding a transcription factor was inserted in a forward direction was isolated, and a DNA construct containing a chimera gene of the gene encoding a transcription factor and SRDX was obtained.

2. Introduction of Transforming Vector into *Agrobacterium*

DNA fragments containing the two att sites, the CaMV35S promoter, the chimera gene, and the NOS-ter of the DNA construct were inserted into a plant transforming vector pBIGCKH (see Patent Literature 7). For this recombination, Gate Way® and LR Clonase® (Invitrogen) were used.

To a mixture of 1.5 µl (approximately 300 ng) of the DNA construct thus obtained and 4.0 µl (approximately 600 ng) of pBIGCKH, 4.0 µl of LR buffer diluted 5 times and 5.5 µl of TE buffer solution (10 mM Tris-Cl (pH 7.0), 1 mM EDTA) were added. 4.0 µl of LR clonase was added to the obtained solution, and the resultant was incubated at 25° C. for 60 min. Subsequently, 2.0 µl of protein kinase K was added, and the resultant was incubated at 37° C. for 10 min. *Escherichia coli* (DH5α etc.) to which 1-2 µl of the obtained solution was introduced was cultivated in a culture solution containing kanamycin so as to select *Escherichia coli* to which a marker gene was introduced. From the *Escherichia coli*, there was prepared a plant transforming vector, which was obtained by successfully inserting, into pBIGCKH, DNA fragments of the DNA construct having the two att and a region between the two att. The vector thus obtained was introduced into strains of soil bacteria (*Agrobacterium tumefaciens* Strain GV3101 (C58C1Rifr) pMP90 (Gmr) (koncz and Sahell 1986)).

3. Transformation of Plant and Collection of T1 Seeds

Using 1 liter of a YEP culture medium or an LB culture medium containing an antibiotic (50 µg/ml of kanamycin (Km), 25 µg/ml of gentamicin (GM), and 50 µg/ml of rifampicin (Rif), *Agrobacterium* to which the above vector had been inserted was cultured. The culture was carried out until OD600 of the culture solution became 1, and then the bacterial cells were collected from the culture solution and suspended in 1 liter of a culture medium for infection (infiltration medium) (see Patent Literature 7). *Arabidopsis thaliana* cultured for 14 days or more was immersed in the bacterial cell suspension for 2 min so that the *Arabidopsis thaliana* was infected with the bacterial cells of *Agrobacterium* to which the transforming vector had been introduced. The *Arabidopsis thaliana* thus transformed was cultured to obtain T1 seeds.

4. Selection of Transformant and Collection of T2 Seeds

The T1 seeds were subjected to sterilization for 7 min with a solution of 25% bleach and 0.02% Triton X-100, and then rinsed three times with sterilized water, and were sown on a sterilized hygromycin selection medium (see Patent Literature 7). From rosette leaves of *Arabidopsis thaliana* obtained by growing the sown T1 seeds, genome DNA was extracted using Nucleon Phytopure (GE Healthcare). Specifically, freeze-dried plant tissues were crushed into powder with dry ice or liquid nitrogen (breaking-down of cell walls). The crushed tissues were removed to a tube, Reagent I was added, and the resultant was suspended, and then Reagent II was added and the resultant was inverted and mixed (lysis of cells). The tube was shaken at 65° C. for 10 min in a water bath, and then left on ice for 20 min. The tube was taken from the ice, chloroform and PhytoPure resin were added, and then the resultant was shaken at room temperature for 10 min. The tube was subjected to centrifugation at 1,300×g for 10 min, and then the supernatant was collected (extraction of DNA). To the collected supernatant was added cold isopropanol in the same amount as that of the collected supernatant, and the resultant was inverted and mixed, subjected to centrifugation at 4,000×g for 5 min, and then the supernatant was removed. The precipitate was washed with cold 70% ethanol, subjected to centrifugation at 4,000×g for 5 min, and the supernatant was removed. The precipitate was dried by wind for 10 min, and a suitable amount of a TE buffer solution or water was added to obtain a DNA solution. Using a genome DNA as a template, PCR was carried out with a primer for a DNA sequence of CaMV35S promoter (GAAGTCATTTCATTTGGAGAGG: SEQ ID No. 22) and a primer for NOS-ter (AGACCGGCAACAGGATTCAATC: SEQ ID No. 23). A plant having the genome DNA amplified by this PCR was selected as a target transgenic plant. T2 seeds were obtained from the selected transgenic plant.

5. Evaluation of Salt Tolerance

T2 seeds of the transgenic plant were sown on an MS culture medium containing 225 mM of NaCl, and the states of seedlings after 3 weeks were evaluated (first selection). It should be noted that under this condition, all wild-type plants die. In order to confirm reproducibility, a further verification test was carried out. MS culture media with four different salt concentrations (Sodium Chloride; 0-250 mM) were prepared, T2 seeds of the transgenic plants and seeds of wild-type plants were sown, and comparison in the state of growth between the T2 seeds and the wild type seeds was made after approximately one month.

FIG. 1 shows the states of growth of breeds which could grow in culture media having a salt concentration (250 mM NaCl) at which wild type *Arabidopsis thaliana* cannot grow.

FIG. 1 shows states of wild type *Arabidopsis thaliana* and *Arabidopsis thaliana* expressing a salt-tolerance chimeric repressor, which were three weeks after sowing on MS plates with various salt concentrations. In the drawing, the uppermost row shows wild type *Arabidopsis Thaliana* (WT), the second row shows At4g21440 (MYB102) chimeric repressor (HR0522) plants, the third row shows At3g04070 (ANAC047) chimeric repressor (CR242) plants, and the lowermost row shows At1g13300 chimeric repressor (HR0237) plants. Panels in each row show, from the left, plants growing on an MS culture medium with a normal composition, an MS culture medium containing 150 mM of NaCl, an MS culture medium containing 200 mM of NaCl, and an MS culture medium containing 250 mM of NaCl, respectively.

The salt concentration used here (250 mM NaCl) was sufficiently high as a salt concentration at which a salt tolerance of a plant was evaluated. It is found from the test that under such a salt concentration, transgenic plants (HR0522, CR242, and HR0237) containing chimeric repressors derived from the three kinds of transcription factors (AT4G21440, AT3G04070, and AT1G13300, respectively) can growth. This shows that the chimeric repressors derived from the three kinds of transcription factors are effective in producing plants capable of standing up to salt damage.

6. Evaluation of High Osmotic Pressure Tolerance

T2 seeds were sown on MS culture media containing 600 mM of mannitol and the states of seedlings after three weeks were evaluated (first selection). It should be noted that under this condition, all wild-type plants die. In order to confirm reproducibility, a further verification test was carried out. MS culture media with four different mannitol concentrations (500-650 mM) were prepared, T2 seeds of the transgenic plants and seeds of wild-type plants were sown, and comparison in the state of growth between the T2 seeds and the wild type seeds was made after approximately one month.

Figure 2:
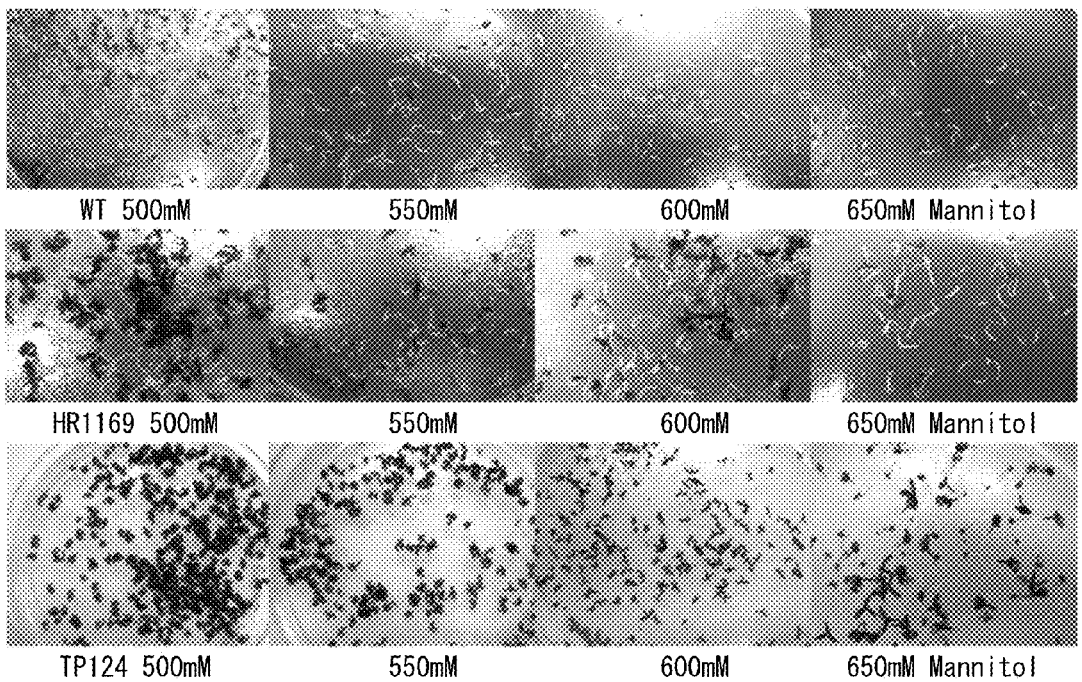
FIG. 2 shows states of wild type *Arabidopsis thaliana* and *Arabidopsis thaliana* expressing an osmotic pressure-tolerance chimeric repressor, which were three weeks after sowing with various mannitol concentrations.

FIG. 2 shows the states of growth of breeds which could grow in culture media having a mannitol concentration (650 mM) at which wild type *Arabidopsis thaliana* cannot grow.

FIG. 2 shows states of wild type *Arabidopsis thaliana* and *Arabidopsis thaliana* expressing an osmotic pressure-tolerance chimeric repressor, which were three weeks after sowing on MS plates with various mannitol concentrations. In the drawing, the uppermost row shows wild type *Arabidopsis Thaliana* (WT), the second row shows AT5G04340 (ZAT6) chimeric repressor (HR1169) plants, and the third row shows AT5G47230 (ATERF5) chimeric repressor (TP124) plants. Panels in each row show, from the left, plants growing on an MS culture medium containing 500 mM mannitol, an MS culture medium containing 550 mM mannitol, an MS culture medium containing 600 mM mannitol, and an MS culture medium containing 650 mM mannitol, respectively.

All wild-type plants die in a culture medium containing 600 mM mannitol. However, it was found from the test that even under such a condition, transgenic plants (HR1169 and TP124) having chimeric repressors derived from the two kinds of transcription factors (AT5G04340 and AT5G47230, respectively) can grow. Since the condition of a high osmotic pressure can be regarded as a stressed condition due to dryness, the chimeric repressors having the two kinds of transcription factors are considered as effective in preventing global warming from having an influence on plants.

The present invention is not limited to the description of the embodiments above, but may be altered by a skilled person within the scope of the claims. An embodiment based on a proper combination of technical means disclosed in different embodiments is encompassed in the technical scope of the present invention.

All the academic literatures and patent literatures cited in the specification are incorporated herein for reference.

INDUSTRIAL APPLICABILITY

The present invention enables producing plants with a stress tolerance such as a salt tolerance and a high osmotic pressure tolerance. Accordingly, the present invention can greatly contribute to the increase in food production. Further, the present invention is effective in producing plants capable of standing up to salt damage and in preventing global warming from having an influence on plants.

The invention claimed is:

1. A method for producing a plant with an increase in high osmotic pressure tolerance, comprising
   introducing into a plant a sequence encoding a fusion protein comprising a first polypeptide and a second polypeptide, wherein the first polypeptide comprises the amino acid sequence set forth in SEQ ID NO: 8 and the second polypeptide comprises the amino acid sequence set forth in SEQ ID NO: 21, wherein the expression of the fusion protein causes transcription of a target gene of the first polypeptide to be inhibited in the plant; and
   selecting a plant for an increase in high osmotic pressure tolerance in comparison to the osmotic pressure tolerance of a plant not comprising said fusion protein.

* * * * *